United States Patent [19]

Fukuoka et al.

[11] Patent Number: 4,547,322

[45] Date of Patent: Oct. 15, 1985

[54] METHOD FOR MANUFACTURE OF DIPHENYLMETHANE DIISOCYANATES

[75] Inventors: Shinsuke Fukuoka; Masazumi Chono; Tomonari Watanabe, all of Okayama; Masashi Kohno, Tokyo, all of Japan

[73] Assignee: Asahi Kasei Kogyo Kabushiki Kaisha, Japan

[21] Appl. No.: 590,671

[22] Filed: Mar. 19, 1984

[30] Foreign Application Priority Data

Mar. 18, 1983 [JP] Japan .................................. 58-45761

[51] Int. Cl.$^4$ ............................................ C07C 118/00
[52] U.S. Cl. ................................... 260/453 P; 560/25
[58] Field of Search ........................ 260/453 P; 560/25

[56] References Cited

U.S. PATENT DOCUMENTS

| | | | |
|---|---|---|---|
| 4,146,727 | 3/1979 | Shawl et al. | 560/25 |
| 4,292,254 | 9/1981 | Leonard | 260/453 P |
| 4,307,029 | 12/1981 | Takeuchi et al. | 260/453 P |
| 4,319,018 | 3/1982 | Miyata et al. | 560/25 X |
| 4,349,484 | 9/1982 | Merger et al. | 260/453 P |
| 4,369,141 | 1/1983 | Motier | 260/453 P |

*Primary Examiner*—Dolph H. Torrence

*Attorney, Agent, or Firm*—Sughrue, Mion, Zinn, Macpeak and Seas

[57] ABSTRACT

Manufacture of a diphenylmethane diisocyanate for an N-phenylcarbamate is economically accomplished in high yield with high selectivity by a method which comprises (A) a process of methylenation for the formation of a condensation product containing at lest 80 mol % of a dinuclear diphenylmethane dicarbamate by the steps of (1) causing a methylenating agent to react upon at least 2 moles of an N-phenylcarbamate, based on 1 mole of the methylene group of said methylenating agent, in a liquid phase in the presence of an aqueous inorganic acid solution, (2) separating the resultant reaction mixture into the aqueous inorganic acid solution and an organic phase reaction mixture containing substantially none of said inorganic acid, and (3) subsequently treating said organic phase reaction mixture in the presence of an N-phenylcarbamate and a carboxylic acid having a pKa of not more than 4 in an aqueous solution at a temperature of 25° C. or a solid acid or an acid consisting of said two acids thereby converting a reaction intermediate possessing a methylene-amino bond and contained in said organic phase reaction mixture to a diphenylmethane dicarbamate, and (B) a process of thermal decomposition described herein.

25 Claims, No Drawings

METHOD FOR MANUFACTURE OF DIPHENYLMETHANE DIISOCYANATES

FIELD OF THE INVENTION

This invention relates to a method for economically manufacturing diphenylmethane diisocyanates in high yields from N-phenylcabamates.

BACKGROUND OF THE INVENTION

The mixture consisting of diphenylmethane diisocyanate (hereinafter referred to as "MDI") and polymethylene polyphenyl isocyanate (hereinafter referred to as "PMPPI"), a higher homolog of MDI, is popularly called "crude MDI" and is mass-produced on a commercial scale as an important raw material for polyurethanes.

The aforementioned dinuclear substance, MDI, is mainly composed of 4,4'-diphenylmethane diisocyanate (namely, pure MDI) and is generally isolated from crude MDI by distillation. In recent years, the demand for this dinuclear MDI as the raw material such as for polyurethane elastomer, Spandex, synthetic leather coating agent, and reaction injection molding polyurethane is rapidly increasing. Accordingly, the desirability of developing a method capable of economically producing the crude MDI containing the dinuclear MDI in a high concentration and entraining other isomers than the 4,4'-isomer in a relatively low concentration has been finding growing recognition.

For the production of this crude MDI, for example, there has been adopted the method which obtains the desired crude MDI by causing condensation of aniline with formaldehyde in the presence of an acid catalyst thereby forming a mixture consisting of diphenylmethane diamine and polymethylene polyphenylamine (hereinafter referred to as "crude MDA"), subsequently allowing phosgene to react upon the crude MDA in a solvent thereby deriving a corresponding carbamic acid choride, then converting the carbamic acid chloride through thermal decomposition into crude MDI and hydrogen chloride, and expelling from the resultant reaction mixture both hydrogen chloride and the reaction solvent.

For the production of crude MDA containing dinuclear diphenylmethane diamine (hereinafter referred to as "MDA") in a high concentration, this conventional method must rely on the use of aniline and an acid catalyst such as hydrochloric acid both in large excesses relative to formaldehyde. Consequently, the amount of base which must be used for the purpose of neutralization is inevitably large. Besides, the recovery of the unaltered aniline is costly. Thus, the method proves to be uneconomical. Moreover, this method has the disadvantage that in spite of an increase in the proportion of the dinuclear component in the crude MDA, the proportion of the 4,4'-isomer in the dinuclear component decreases and the proportions of the rather unwanted isomers, i.e. 2,4'-MDA and 2,2'-MDA, are increased.

Further, this conventional method is disadvantageous in that the process involved necessitates the use of violently poisonous phosgene, that the use of phosgene entails generation of corrosive hydrogen chloride in a large volume, that the final product entrains hydrolyzable chlorine compounds, and that these by-productss are extremely difficult to separate away. For the purpose of eliminating all these drawbacks, research is under way in search of new processes capable of producing MDI without the use of phosgene.

As one solution for the elimination of the use of phosgene, for example, the method which comprises causing condensation of N-phenylcarbamate with formaldehyde thereby giving rise to a mixture consisting of diphenylmethane dicarbamate and polymethylene polyphenylcarbamate, a higher homolog of diphenylmethane dicarbamate,, ad subsequently subjecting this mixture to thermal decomposition has been proposed (U.S. Pat. Nos. 4,349,484 and 4,307,029 and European Patent Nos. 28,337 and 30,039).

These methods under development for the aforementioned purpose, however, are such that the proportions of the dinuclear MDI in the produced crude MDI fall roughly in a low range of 40 to 78%, the range virtually comparable with the range usual with the process using phosgene. Thus, these methods are not satisfactory.

Various other methods have been proposed which produce condensation mixtures consisting of diphenylmethane dicarbamates and their higher homologs by the condensation of N-phenylcarbamates with formaldehydes. For example, the method which resorts to the reaction of N-phenylcarbamates with condensing agents such as formaldehyde, paraformaldehyde, methylal, and trioxane in the presence of various acids such as mineral acids and organic sulfonic acids. If relatively severe conditions are used in this reaction, for example, if a strong acid is used in a large amount, the reaction temperature is high or the reaction period is extended, not only is the desired diphenylmethane dicarbamate produced but also polynuclear polymethylene polypenylcarbamates having the following formula are produced in a significant amount:

NHCOOR (wherein R is an alkyl group, aromatic group or an alicyclic group; z is an integer of 1 or more). Furthermore, if a strong liquid acid is used, much difficulty and hence a lot of cost is entailed in separating the acid from the reaction mixture and recovering the same in a reusable form.

In order to eliminate this defect with the recovery of acids, a method was proposed for using an aqueous acid solution having a concentration of 10% or higher (British Patent No. 2,044,252, Japanese Patent (OPI) Nos. 81850/80 and 81851/80 and Chemical Abstracts 93 169057e). This method is effective for acid recovery because as shown in the working examples, if aqueous acid solutions having a concentration of not more than 50% are used, the acid can fairly easily be separated from the organic phase in the form of layers. However, the presence of a great amount of water renders it difficult to complete the reaction without leaving a significant amount of compounds having a methylene-amino bond(—$CH_2$—N<) wherein the methylene group is bonded to the nitrogen atom in the carbamate group. In order to complete the reaction without these compounds, less water must be used to increase the acid concentration to, for example, 80% or higher. However, this causes the hydrolysis of the starting compound or the reaction product, or leaves them to dissolve in the concentrated aqueous acid solution in a large quantity, and as a result, the separation of the product from the acid solution becomes difficult.

In any event, it is not industrially advantageous to carry out a one-step condensation of N-phenylcarbamates with an aqueous solution of acid and to use the resulting product in the preparation of isocyanates. More specifically, dinuclear, trinuclear or other polynuclear compounds having the methylene-amino bond cannot be easily separated from the condensation product containing diphenylmethane dicarbamates and polymethylene polyphenylcarbamates. If the condensation product containing these compounds with the methylene-amino bond is decomposed thermally, these compounds do not provide the desired isocyanates. Furthermore, they enter into various side reactions with the isocyanates derived from the carbamates such as diphenylmethane dicarbamates, and in consequence, the yields of the desired isocyanates are reduced. In addition, the resulting by-products cannot be easily separated from the desired isocyanates, particularly, the polynuclear polymethylene polyphenyl isocyanates, and they are in all cases present in the final product generally referred to as a polymeric isocyanate, and properties of the product are impaired.

It is therefore necessary to perform the condensation of N-phenylcarbamates in such a manner that a minimum amount of the compounds with the methylene-amino bond is left in the condensation product. One method that has been proposed for attaining this object is described in U.S. Pat. No. 4,146,727, wherein these compounds with the methylene-amino bond are subjected to a rearrangement reaction, under substantially anhydrous conditions, with a protonic acid catalyst having a strength of at least the magnitude of a 75% sulfuric acid, or a Lewis acid at a temperature of 50° to 170° C. so as to rearrange the methylene group, which was bonded to the nitrogen atom, to bond to the benzene ring. However, this method must use a large amount of concentrated sulfuric acid or paratoluenesulfonic acid and again requires complicated procedures and great cost for separating and recovering these acids from the reaction mixture.

Japanese Patent (OPI) No. 7749/81 and *Chemical Abstracts*, 94 209480s propose a method for producing polymethylene polyphenylcarbamate by heating only bis(N-carboalkoxyanilino)methane, which is a compound having the methylene-amino bond, in the presence of an acid catalyst. However, this method is not ideal for selective production of the diphenylmethane dicarbamate because it causes not only the desired rearrangement reaction but also the undesired condensation reaction, and trinuclear and other polynuclear polymethylene polyphenylcarbamates are formed as by-products in addition to the desired diphenylmethane dicarbamate. Furthermore, the reaction is slow and the rearrangement reaction is not completed without leaving the residual bis(N-carboalkoxyanilino)methane in the reaction product.

U.S. Pat. No. 4,319,018, British Patent No. 2,054,584, Japanese Patent (OPI) No. 12357/81 and *Chemical Abstracts*, 94, 124715t propose a method for producing diphenylmethane dicarbamates and polymethylene polyphenylcarbamates by reacting N-phenylcarbamates with formaldehyde or its precursor in the presence of both an acid catalyst and the compounds having the methylene-amino bond. However, this method is unable to reduce the content of the compounds with the methylene-amino bond, and the compounds are unavoidably left in the condensation product in an amount as much as ten-odd percent by weight.

SUMMARY OF THE INVENTION

It has been found that the various methods heretofore proposed for producing crude MDI of diphenylmethane dicarbamate and polymethylene polyphenylcarbamates, intermediates for crude MDI, from N-phenylcarbamates without using phosgene have numerous drawbacks which hinder their reduction to commercialization.

Particularly in the case of the methods which have heretofore been proposed for economic production of dinuclear MDI in high yields exceeding 80%, including those involving use of phosgene, none of them has proved completely satisfactory.

The inventors, therefore, continued a diligent study with the object of developing a method capable of economic production of dinuclear MDI in high yields by a novel procedure without using phosgene. They have consequently acquired a knowledge that this object is attained by combining a specific process of methylenation using N-phenylcarbamate as the raw material with a specific process of thermal decomposition. The present invention has been completed based on this knowledge.

To be specific, this invention provides a method for the manufacture of a diphenylmethane diisocyanate from a N-phenylcarbamate, comprising:

(A) a process of methylenation for the formation of a condensation product containing at least 80 mol % of a dinuclear diphenylmethane dicarbamate by the steps of
  (1) causing a methylenating agent to react upon at least 2 moles of a N-phenylcarbamate, based on 1 mole of the methylene group of the methylenating agent, in a liquid phase in the presence of an aqueous inorganic acid solution.
  (2) separating the resultant reaction mixture into the aqueous inorganic acid solution and an organic phase reaction mixture containing substantially none of the aforementioned inorganic acid, and
  (3) subsequently treating the aforementioned organic phase reaction mixture in the presence of a N-phenylcarbamate and a carboxylic acid having the Pka value of not more than 4 in an aqueous solution at a temperature of 25° C. and/or a solid acid thereby converting a reaction intermediate possessing a methylene-amino bond contained in the aforementioned organic phase reaction mixture to a diphenylmethane dicarbamate, and (B) a process of thermal decomposition by the steps of allowing a mixture comprising 1 to 50% by weight of the condensation product obtained in the preceding process of (A) and 99 to 50% by weight of a thermal decomposition solvent having a boiling point under atmospheric pressure in the range of 120° to 350° C. and being inactive to isocyanates to flow down into a reactor maintained at temperature in the range of 180° to 380° C. through the upper part thereof, causing the mixture to come into counterflow contact with a carrier introduced into the reactor upwardly via the lower part thereof thereby producing an organic hydroxyl compound, allowing the organic hydroxyl compound to be discharged from the reactor in the form of vapor in conjunction with the carrier through the upper part thereof, and withdrawing the resultant isocyanate solution from the reactor through the lower part thereof.

As described above, by the method of this invention, the dinuclear diphenylmethane dicarbamate is produced from the N-phenylcarbamate in yields of at least 80% and then MDI is produced in high yields with high selectivity by allowing the condensation product obtained as described above to flow down into a thermal decomposition reactor through the upper part thereof in the presence of a solvent and causing the introduced condensation product to come into counterflow contact with the carrier introduced upwardly into the reactor through the lower part thereof thereby causing thermal decomposition of the condensation product.

Further, since the thermal decomposition is carried out in such a specific manner as described above and since the carbamate subjected to the thermal decomposition is composed mainly of the diphenylmethane dicarbamate, a dinuclear substance, the method of this invention is characterized by suffering the formation of any by-products only minimally during the process of thermal decomposition, enabling the reaction of thermal decomposition reaction to proceed at a high rate, and permitting the decomposition to be carried out easily in an industrially advantageous continuous operation.

Moreover, the method of this invention is characterized by the fact that the process of methylenation is commercially advantageous because it not only produces the dinuclear diphenylmethane dicarbamate in high yields but also permits the catalyst used therein to be easily separated from the reaction mixture and put to reuse.

DETAILED DESCRIPTION OF THE INVENTION

The N-phenylcarbamates used in the process of the present invention are the compounds represented by formula (I):

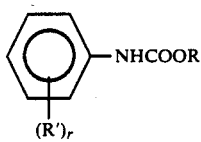

(I)

wherein R is an alkyl group having from 1 to 20 carbon atoms, preferably from 1 to 10 carbon atoms, aromatic group or an alicyclic group having 3 to 30 carbon atoms, preferably from 5 to 18 carbon atoms; R' is hydrogen or a substituent such as an alkyl group having from 1 to 20 carbon atoms, halogen atom, nitro group, cyano group, alkoxy group having from 1 to 20 carbon atoms or alicyclic group having from 3 to 20 carbon atoms, provided that these substituents are bonded at the ortho- or meta-position to the urethane group; r is an integer of 0 to 4; when r is 2 or more, R' may represent the same or different substituents; and at least one hydrogen in R may be substituted by any of the substituents listed above.

Preferred examples of R include alkyl groups such as methyl, ethyl, 2,2,2-trichloroethyl, 2,2,2-trifluoroethyl, propyl (n- or iso-), butyl (n- and various isomers), pentyl (n- and various isomers) and hexyl (n- and various isomers), alicyclic groups such as cyclopentyl and cyclohexyl and aromatic groups such as phenyl and naphthyl; and preferred examples of R' include hydrogen, the alkyl groups and alicyclic groups listed above, halogens such as fluorine, chlorine, bromine and iodine, nitro groups, cyano groups and alkoxy groups having the alkyl moieties listed above.

Preferred examples of the N-phenylcarbamates represented by formula (I) include methyl N-phenylcarbamate, ethyl N-phenylcarbamate, propyl N-phenylcarbamate (its isomers), butyl N-phenylcarbamate (its isomers), pentyl N-phenylcarbamate (its isomers), hexyl N-phenylcarbamate (its isomers), cyclohexyl N-phenylcarbamate, 2,2,2-trichloroethyl N-phenylcarbamate, 2,2,2-trifluoroethyl N-phenylcarbamate, methyl N-o- (or m-)tolylcarbamate, ethyl N-o- (or m-)tolylcarbamate, 2,2,2-trifluoroethyl N-o- (or m-)tolylcarbamate, propyl N-o- (or m-)tolylcarbamate (its isomers), butyl N-o- (or m-)tolylcarbamate (its isomers), methyl N-o- (or m-)chlorophenylcarbamate, ethyl N-o- (or m-)chlorophenylcarbamate, propyl N-o- (or m-)chlorophenylcarbamate (its isomers), butyl N-o- (or m-)chlorophenylcarbamate (its isomers), 2,2,2-trifluoroethyl N-o- (or m-)chlorophenylcarbamate, methyl N-2,6-dimethylphenylcarbamate, ethyl N-2,6-dimethylphenylcarbamate, propyl N-2,6-dimethylphenylcarbamate (its isomers), butyl N-2,6-dimethylphenylcarbamate (its isomers), 2,2,2-trifluoroethyl N-2,6-dimethylphenylcarbamate, methyl N-2,6-dibromophenylcarbamate, ethyl N-2,6-dibromophenylcarbamate, propyl N-2,6-dibromophenylcarbamate (its isomers), butyl N-2,6-dibromophenylcarbamate (its isomers), and 2,2,2-trifluoroethyl N-2,6-dibromophenylcarbamate.

The present invention does not discriminate with respect to the N-phenylcarbamate to be used as the raw material by the method by which it is produced. Examples of the method by which this raw material is produced include a method which resorts to reductive alkoxycarbonylation of a suitable aromatic nitro compound with carbon monoxide and an alcohol, a method which resorts to reaction of a suitable aromatic amine with a chloroformic ester, a method which resorts to interamination of a suitable aromatic amine and an N-unsubstituted carbamate, a method which resorts to reaction of a suitable aromatic amine with an alcohol and a urea, and a method which resorts to oxidative alkoxycarbonylation of a suitable aromtic amine and/or N,N'-diaryl urea with carbon monoxide and an alcohol in the presence of an oxidizing agent.

From the standpoint of commercialization, the method resorting to the oxidative alkoxycarbonylation of an aromatic amine and/or N, N'-diaryl urea proves particularly advantageous over any other of the methods cited. Concerning the production of N-phenylcarbamates by this particular method, the inventors have already developed a catalyst system which assists in producing the N-phenylcarbamate in high yields with high selectivity, permits the reaction to proceed quickly, enables itself to be easily recovered from the reaction mixture and put to recurrent use, and enables the production of the N-phenylcarbamate to be carried out quite economically (European Patent No. 83,096).

This catalyst for the oxidative alkoxycaronylation comprises:

(a) at least one member selected from the group consisting of platinum group metals and compounds containing at least one platinum group element; and (b) at least one halogen-containing compound selected from the group consisting of alkali or alkaline earth metal halides, onium halides, compounds capable of forming onium halides in the reaction, oxo acids of halogen atoms and their salts, complex compounds containing halogen ions, organic halides and halogen molecules.

One particularly preferred embodiment of the invention relating to this catalyst resides in the use of a catalyst system which comprises metallic palladium and an iodine compound (such as an alkali metal iodide or quaternary ammonium iodide).

Illustrative methylenating agents that can be used in the present invention include formaldehyde, paraformaldehyde, trioxane, tetraoxane, dialkoxymethane, diacyloxymethane, 1,3-dioxolane, 1,3-dioxane, 1,3-dithiane, 1,3-oxathiane, and hexamethylenetetramine. Preferred compounds are formaldehyde, paraformaldehyde, trioxane and dialkoxymethanes having the lower alkyl groups of 1 to 6 carbon atoms such as dimethoxymethane, diethoxymethane, dipropoxymethane, dipentanoxymethane and dihexyloxymethane, as well as diacyloxymethanes having the lower acyloxy groups such as diacetoxymethane and dipropioxymethane. These methylenating agents may be used either alone or in combination. A particularly preferred methylenating agent is an aqueous solution of formaldehyde. One feature of the present invention is its ability to produce diphenylmethane dicarbamates in high selectivity using the least expensive methylenating agent such as an aqueous formaldehyde.

This process of methylenation is started by the first step which causes a N-phenylcarbamate to react with the aforementioned methylenating agent at a temperature in the range of 40° to 150° C. by using an aqueous inorganic acid solution as a catalyst. Suitable inorganic acids include hydrochloric acid, sulfuric acid, phosphoric acid, polyphosphoric acid, heteropolyacid and boric acid. Sulfuric acid is particularly preferred. The concentration of the inorganic acid in its aqueous solution preferably ranges from 20 to 70 wt %, and the range of 30 to 60 wt % is particularly preferred. The most preferred is an aqueous solution containing 40 to 60 wt % of sulfuric acid. If the concentration of the inorgnic acid exceeds 70 wt %, the N-phenylcarbamate and the condensation products are hydrolyzed to form the corresponding amino compounds. These amino compounds are not desirable since it causes various bad side reactions when the diphenylmethane dicarbamate produced is subsequently converted to an isocyanate by thermal decomposition. Furthermore, such a highly concentrated acid solution dissolves a significant amount of the starting materials and the reaction product therein, so that the separation of the organic phase from the mixture is performed only with complicated procedures. On the other hand, if the concentration of the inorganic acid is less than 20 wt %, the reaction is too slow to suit practical purposes.

In the first reaction step of the methylenation process, at least 2 mols, preferably 2.2 to 10 mols, more preferably 2.5 to 6 mols, of the N-phenylcarbamate is used per mol equivalent of the methylene group of the methylenating agent. The aqueous solution of inorganic acid is used in such an amount that it preferably contains 0.01 to 20 mol equivalents, more preferably 0.05 to 15 mol equivalents, most preferably 0.1 to 10 mol equivalents, of the inorganic acid per mol equivalent of the N-phenylcarbamate.

The first reaction step of the methylenation process may be performed in a two-component dispersion made of organic and aqueous phases using water as the reaction medium. Alternatively, the reaction may be performed in a two-component dispersion made of an aqueous phase and an organic phase using an organic solvent. In either case, it is preferred that the most finely dispersed liquid droplets be formed throughout the reaction. Preferred organic solvents are those which have boiling points of not higher than 300° C. at atmospheric pressure and which have a mutual solubility with water of not more than 10% at room temperature. If organic solvents having a mutual solubility with water of not more than 10% are used, the organic phase containing the diphenylmethane dicarbamate and other condensates can be readily separated from the aqueous phase containing the inorganic acid by simple means such as phase separation after the first reaction. If, on the other hand, organic solvents having boiling points of not higher than 300° C. at atmospheric pressure are used, these solvents can be separated from the organic-phase reaction mixture by simple means such as distillation.

Preferred organic solvents include aromatic compounds having electron attracting substituents or halogen atoms. Suitable electron attracting substituents include nitro, cyano, alkoxycarbonyl, sulfonate, trifluoromethyl and trichloromethyl groups. These aromatic compounds are substantially inert to the electrophilic substitution of the methylene group under the conditions used for the first reaction step of the methylenation process. Furthermore, these aromatic compounds have great ability to dissolve not only the N-phenylcarbamates (used as one of the starting materials) but also the diphenylmethane dicarbamates finally produced.

A particularly preferred electron attracting group is a nitro group. Preferred examples of the aromatic compounds having a nitro group or a halogen atom or both include nitrobenzene and lower alkyl substituted nitrobenzenes such as nitrotoluene (its isomers), nitroxylene (its isomers), nitromesitylene and nitroethylbenzene (its isomers); halogen substituted nitrobenzenes such as chloronitrobenzene (its isomers) and bromonitrobenzene (its isomers); halogenated benzenes such as chlorobenzene, dichlorobenzene (its isomers), trichlorobenzene (its isomers), bromobenzene, dibromobenzene (its isomers) and tribromobenzene (its isomers); halogenated naphthalenes such as chloronaphthalene (its isomers), dichloronaphthalene (its isomers) and bromonaphthalene (its isomers); and lower alkyl substituted halogenated benzenes such as chlorotoluene (its isomers), dichlorotoluene (its isomers), ethyl chlorobenzene (its isomers), chloroxylene (its isomers), bromotoluene (its isomers) and bromoxylene (its isomers). Particularly preferred organic solvents are nitrobenzene, chlorobenzene, and dichlorobenzene (its isomers).

In the first reaction step of the methylenation process, the reaction is carried out at a temperature in the range of 40° to 150° C., preferably 60° to 130° C., more preferably 70° to 110° C. The pressure used herein is in the range of 0.5 to 20 kg/cm², preferably 0.8 to 10 kg/cm². Generally, the reaction is carried out under atmospheric pressure or under a low pressure. The reaction period varies with the type, the concentration and the amount of the aqueous solution of inorganic acid and the reaction temperature. The reaction period also depends on whether any organic solvent is used, or on the type of the reactor used. Since it is preferred that the smallest possible amount of the methylenating agent is left in the reaction mixture coming out of the first reaction step of the methylenation process, the duration of the first reaction generally ranges from several minutes to several hours, preferably 10 minutes to 6 hours, more preferably 0.5 to 3 hours. The reaction may be performed either batchwise or continuously.

The reaction mixture obtained in the first reaction step of the methylenation process is separated into the aqueous solution of inorganic acid and an organic-phase reaction mixture substantially free from the inorganic acid, and it is preferable that resulting aqueous solution of inorganic acid is returned to the first reaction step either immediately or after the adjustment of the aqueous solution of inorganic acid to the predetermined concentration if necessary.

While there is no particular limitation on the method of separating the aqueous solution of inorganic acid from the organic-phase reaction mixture, the simple phase-separation technique can be used for the purpose under the conditions specified for the present invention. The following phase-separation methods may be used: according to one method, the reaction mixture is cooled, without using an organic solvent, to a temperature close to or lower than room temperature, and in this case, the organic-phase reaction mixture forms a solid phase and can be readily separated from the aqueous solution of inorganic acid by simple means such as filtration. According to the other method, the reaction mixture is dissolved in the organic solvent described above or heated to a temperature over 50°-60° C., and in this case, two immiscible liquid phases (organic phase and aqueous phase) form and can readily be separated from each other.

The organic-phase reaction mixture thus separated from the aqueous solution of inorganic acid may sometimes contain a small amount of the inorganic acid, which is preferably removed by a suitable method such as washing with water. If the inorganic acid remains unremoved from the final condensation product, it causes undesirable side reactions or corrodes the reactor during the subsequent thermal decomposition of the condensation product for producing the isocyanates.

The concentration of the inorganic acid in its aqueous solution that has been separated from the organic-phase reaction mixture in the separation step is generally lower than the initial value because water is produced in the first reaction step of the methylenation process if a formaldehyde is used as the methylenating agent, and if an aqueous solution of formaldehyde is used, there is also a corresponding increase in the water content. Therefore, if one wants to perform the first reaction under constant conditions, the concentration of the inorganic acid must be increased to a predetermined level for re-use. For the purposes of the present invention, the preferred concentration of the inorganic acid solution used in the first reaction step of the methylenation process ranges from 20 to 70 wt %, and a particularly preferred range is from 30 to 60 wt %. As the concentration of this acid is relatively low, the concentration can be readily attained by dehydration with less efforts than are required for concentrating a diluted acid solution to a highly concentrated acid. Needless to say, the aqueous solution of inorganic acid separated may be immediately returned to the first reaction step if the concentration of the inorganic acid is within the range described above.

Then, the second reaction step of the methylenation process is carried out. This step comprises subjecting the resultant organic phase reaction mixture containing substantially no inorganic acid to a treatment at a temperature in the range of 40° to 200° C. in the presence of a N-phenylcarbamate and a carboxylic acid having a pka of not more than 4 in an aqueous solution at a temperature of 25° C. and/or a solid acid.

In the subsequent second reaction step of the methylenation process, the reaction is preferably carried out in the presence of a minimum amount of water because water has an undesirable influence on the reactivity of the reactants and the reaction rate. Water is particularly undesirable if a carboxylic acid is used as the catalyst because this must be finally separated from water. Therefore, it is desired that as much water as possible be removed from the organic-phase reaction mixture obtained in the separation step. One method for attaining this object is by azeotropic distillation in the presence of an azeotropic agent. If an organic solvent is used in the first reaction step of the methylenation process, the distillation of the water can be achieved simultaneously with the distillation of a portion of or all of this organic solvent.

In the second reaction step of the methylenation process, the reaction is preferably performed in the substantial absence of a methylenating agent. If the organic-phase reaction mixture that has been subjected to phase separation and optional washing with water still contains a methylenating agent, the methylenating agent is preferably removed simultaneously with the removal of the water from the mixture. However, if formaldehyde or its precursor which generates formaldehyde in the reaction system is used as a methylenating agent, it seldom occurs that such a methylenating agent is left in the organic-phase reaction mixture because formaldehyde or its precursor is in most cases water-soluble.

The organic-phase reaction mixture thus obtained is substantially free from the methylenating agent, but it does contain the intermediate compounds with the methyleneamino bond ($-CH_2-N<$), for example, bis(N-carboalkoxyanilino)methane and (N-carboalkoxyanilinomethyl)phenylcarbamate. The purpose of the second reaction step is to convert these compounds to diphenylmethane dicarbamates by an easy and simple method, and it is essential that in this second reaction step, the reaction must be carried out in the presence of N-phenylcarbamates. This object can be achieved by carrying out the intermolecular transfer reaction of the intermediate compounds with an N-phenylcarbamate.

As described before, one conventional method to convert these intermediate compounds having the methyleneamino bond to diphenylmethane dicarbamates and polymethylene polyphenylcarbamates has been proposed (see U.S. Pat. No. 4,146,727). This method, however, consists of the intramolecular rearrangement and condensation reactions of the intermediate compounds, so that it requires a very strong protonic acid having a strength equal to or greater than a 75% concentrated sulfuric acid or a very strong Lewis acid such as antimony pentafluoride, and it also requires a considerable length of the reaction time, in order to complete the reaction. On the other hand, according to the process of the present invention, the compounds having the methylene-amino bond are subjected to an intramolecular transfer reaction with an N-phenylcarbamate which may be the same as or different from the N-phenylcarbamate used as the starting material. Therefore, the process of the present invention does not require the use of an acid as strong as what is used in the conventional method that depends on intramolecular rearrangement reaction of the compounds having the methylene-amino bond. Instead, the present invention used a much weaker carboxylic acid having a pKa of not more than 4, preferably from 3 to −4, more preferably from 2.5 to −4, in an aqueous solution at 25° C. or solid acid. Even in the presence of this weak acid, the process of the present invention permits the intended reaction to proceed quantitatively at a fast rate, and the desired diphenylmethane dicarbamates can be obtained with high selectivity.

For the sake of clarity, the process of the intermolecular transfer reaction carried out in the second reaction step of the methylenation process is illustrated below with reference to the case where an unsubstituted N-phenylcarbamate is reacted with the compound having the methylene-amino bond:

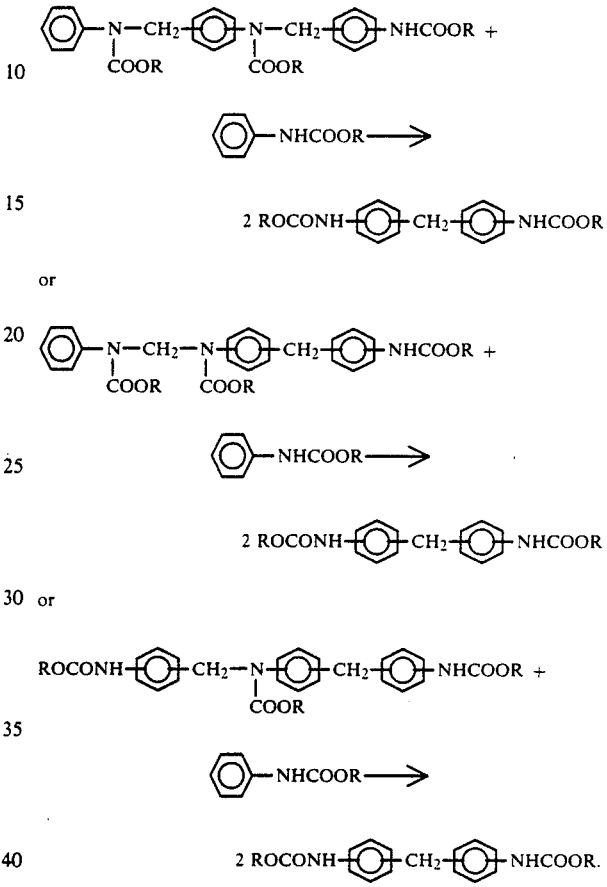

(wherein R″ may be the same or different from R).

As shown above, in the reaction between the dinuclear compound having the methylene-amino bond with the N-phenylcarbamate, the N-phenylcarbamate as one of the reactants is regenerated and a compound wherein R″ is replaced by R is also formed. But in any event, one of the reaction products obtained is a dinuclear diphenylmethane dicarbamate which can be used as a starting material for the production of diphenylmethane diisocyanates. In commercial operation, R and R″ are usually the same and the production of the above mentioned by-product can be avoided.

Further, trinuclear and other polynuclear compounds having the methylene-amino bond can be converted to diphenylmethane dicarbamates as illustrated below.

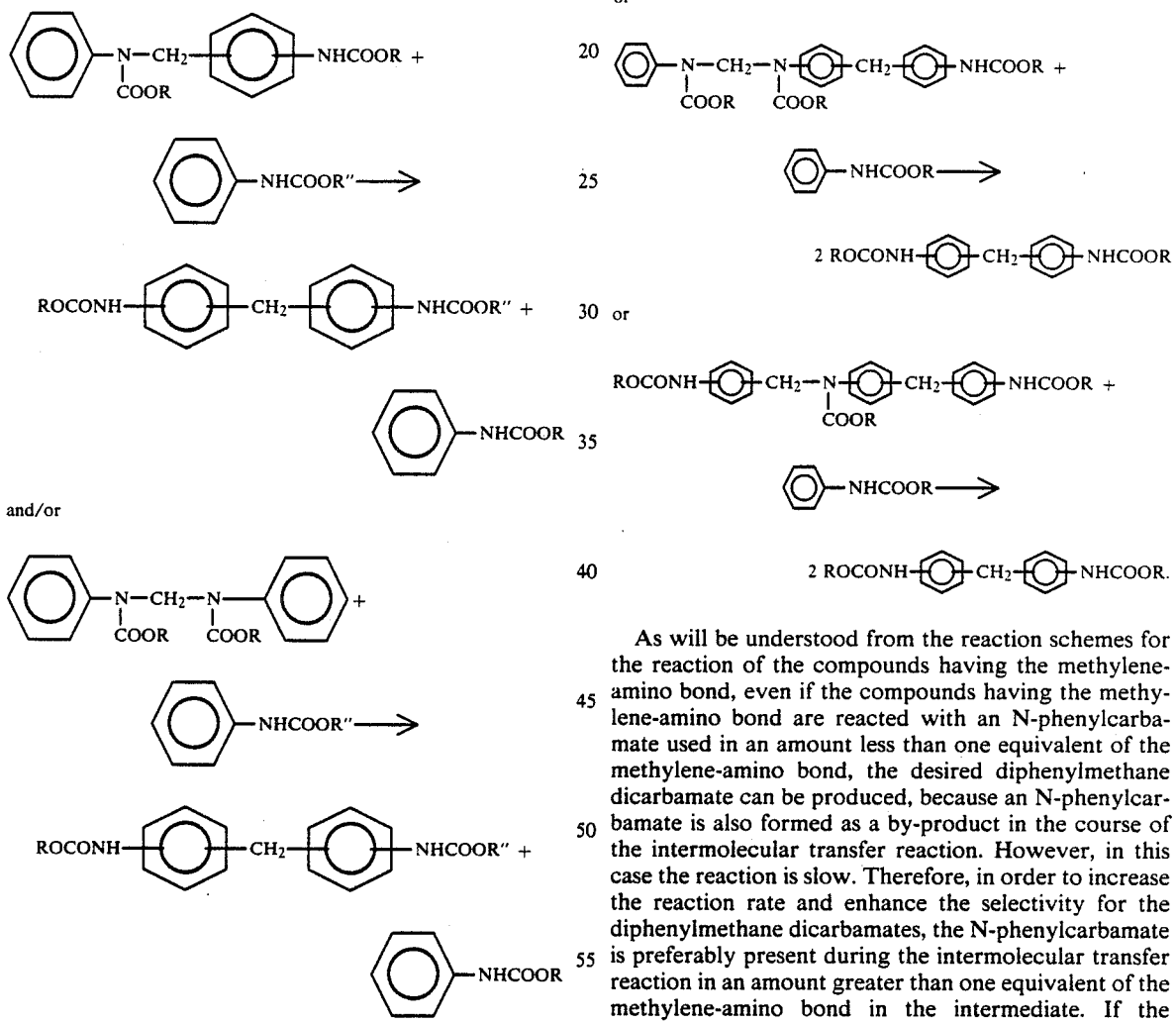

As will be understood from the reaction schemes for the reaction of the compounds having the methylene-amino bond, even if the compounds having the methylene-amino bond are reacted with an N-phenylcarbamate used in an amount less than one equivalent of the methylene-amino bond, the desired diphenylmethane dicarbamate can be produced, because an N-phenylcarbamate is also formed as a by-product in the course of the intermolecular transfer reaction. However, in this case the reaction is slow. Therefore, in order to increase the reaction rate and enhance the selectivity for the diphenylmethane dicarbamates, the N-phenylcarbamate is preferably present during the intermolecular transfer reaction in an amount greater than one equivalent of the methylene-amino bond in the intermediate. If the amount of the N-phenylcarbamate remaining unreacted in the organic-phase reaction mixture is not sufficient for this purpose, an additional amount of the N-phenylcarbamate is preferably incorporated in the second reaction step of the methylenation process. For the purpose, N-phenylcarbamate is preferably present in an amount of from 1 to 200 mol equivalents, more preferably from 5 to 100 mol equivalents, per equivalent of the methylene-amino bond.

As described above, the greatest feature of the second reaction step of the methylenation process is to use at least one catalyst selected from the group consisting of a carboxylic acid which has a pKa or not more than 4 in an aqueous solution at 25° C., and a solid acid. Suitable carboxylic acids meeting this requirement include formic acid; halogenated acetic acids such as fluoroacetic acid, difluoroacetic acid, trifluoroacetic acid, chloroacetic acid, dichloroacetic acid, trichloroacetic acid, bromoacetic acid, dibromoacetic acid, tribromoacetic acid, iodoacetic acid, diiodoacetic acid and triiodoacetic acid; α-halogenated and α,α-dihalogenated aliphatic carboxylic acids such as α-fluoropropionic acid, α,α-difluoropropionic acid, α-chloropropionic acid, α,α-dichloropropionic acid, α-fluorobutyric acid and α-chlorobutyric acid; α-cyano aliphatic carboxylic acids such as cyanoacetic acid, α-cyanopropionic acid and α-cyanobutyric acid; acylacetic acids such as acetoacetic acid, dichloroacetyl acetic acid and fluoroacetyl acetic acid; alkoxy acetic acids and phenoxy acetic acids such as methoxy acetic acid, ethoxy acetic acid, chlorophenoxy acetic acid (its isomers) and cyanophenoxy acetic acid (its isomers); halogenated benzoic acids such as chlorobenzoic acid (its isomers), fluorobenzoic acid (its isomers), difluorobenzoic acid (its isomers), bromobenzoic acid (its isomers) and trichlorobenzoic acid (its isomers); hydroxy benzoic acids such as salicyclic acid, dihydroxy benzoic acid (its isomers) and trihydroxy benzoic acid (its isomers); nitrated benzoic acids such as nitrobenzoic acid and dinitrobenzoic acid; glycolic acid; lactic acid; malic acids such as malic acid, dimethyl malic acid and dihydroxy malic acid; tartaric acids such as tartatic acid, dimethyl tartaric acid and dihydroxy tartaric acid; citric acid; malonic acids such as malonic acid and dimethyl malonic acid; oxalic acid; maleic acid; fumaric acid; mandelic acid; phthalic acids such as phthalic acid (its isomers) and halogenated phthalic acid (its isomers); furancarboxylic acids; thiophencarboxylic acids; thioacetic acid; cyclopropane-1,1-dicarbaoxylic acids; sulfoacetic acids such as sulfoacetic acid and difluorosulfoacetic acid; halogenated malonic acids such as difluoromalonic acid and dichloromalonic acid; and halogenated succinic acids such as 1,2-difluorosuccinic acid, perfluorosuccinic acid and perchlorosuccinic acid. Among these carboxylic acids, halogenated acetic acids, α-halogenated and α,α-dihalogenated aliphatic carboxylic acids are preferred, with halogenated carboxylic acids wherein the halogen is chlorine or fluorine being particularly preferred. Fluorinated carboxylic acids are more preferred, and trifluoroacetic acid is most preferred.

Examples of the solid acid that can be used in the second reaction step of the methylenation process are listed below: acidic clay minerals and inorganic cation exchangers such as acid clay, bentonite, kaolin, zeolite and montmorillonite; these acidic clay minerals and inorganic cation exchangers that have been treated with inorganic acids such as hydrofluoric acid, hydrochloric acid, perchloric acid and sulfuric acid, or ammonium salts of these acidic clay minerals and inorganic cation exchangers which have been subjected to protonation treatment by calcination; the solidified acids that are prepared by supporting liquid acids such as sulfuric acid, phosphoric acid, organic carboxylic acids and organic sulfonic acids or the heteropoly-acids such as dodecamolybdophosphoric acid, dodecamolybdosilicic acid, dodecatungstophosphoric acid, dodecatungstosilicic acid and tungstomolybdophosphoric acid on carriers such as alumina, silica, silica-alumina, silica-alumina-zirconia, zirconia, titania, boria, zeolite, silica-titania, barium sulfate, calcium carbonate, asbestos, bentonite, diatomaceous earth, activated carbon, graphite, activated clay and acidic clay minerals, followed by heat treatment; solid sulfuric acid products that are prepared by first gelling water-soluble sols (e.g., alumina sol, silica-alumina sol and silica sol) in the presence of sulfuric acid, adding a large amount of sulfuric acid to dissolve the gel, and then cooling the solution to solidify, or precipitating a crystal from the solution, or heating the solid obtained to a temperature between 100° and 600° C.; metal oxides and mixed metal oxides such as silica, alumina, zinc oxide, titania, antimony oxide, silica-alumina, silica-titania, titania-alumina, and silica-zirconia; acidic solid sulfates, nitrates and phosphates such as nickel sulfate, aluminum sulfate, iron sulfate, chromium nitrate, bismuth nitrate, zirconium phosphate, aluminum phosphate, and these sulfates, nitrates and phosphates that are supported on the carriers listed above; organic cation exchange resins having at least one acidic group such as fluoroalkyl sulfonic acid group, fluoroalkyl carboxyl group or alkyl phosphoric acid group; and inorganic oxides having either —R'''—SO$_3$H or —R'''—COOH or both bound thereto.

As for the inorganic oxides having —R'''—SO$_3$H or —R'''—COOH bound thereto, those having a divalent organic residual group or organometallic compound residue as R''' and having not more than 30, especially not more than 20, carbon atoms are preferred. Suitable examples of the organic residual group include aliphatic hydrocarbon groups, aromatic hydrocarbon groups, aralkyl hydrocarbon groups, and fluoroalkyl groups, as well as those which have an ether bond, thioether bond, sulfone bond, carbonyl bond, ester bond, amido bond, imido bond or heterocyclic portion at terminal or in the backbone of these hydrocarbon groups. Suitable examples of the organometallic compound residues include those which have a metallic element bound to the terminal or backbone of the organic residual groups listed above. Organosilicon compound residues having a silicon atom at terminal, for example, those having a halosilyl or alkoxysilyl group bound to the terminal are advantageous because they are easy to prepare and form a stable bond with inorganic oxides.

The organic residual groups or organometallic compound residues listed above may have part of the hydrogen atoms present replaced by a halogen atom such as fluorine, chlorine or bromine, or substituents such as alkyl, alkoxy, aryl, aryloxy, hydroxyl, nitrile, alkoxycarbonyl, carboxyl, and sulfonic acid groups. Advantageous inorganic oxides include those having a hydroxyl group on the surface such as silica, silica-alumina, alumina, titania, zirconia, magnesia, zeolite, diatomaceous earth, clay materials, glass, titania-alumina, silica-titania and silica-zirconia. Silica, porous glass and silica-alumina are particularly preferred.

Preferred examples of the solid acids include acidic clay minerals and inorganic cation exchangers, or these acidic solid materials that have been subjected to acid or protonation treatment; acidic metal oxides and mixed metal oxides, or these acidic solid materials that have been subjected to acid or protonation treatment; organic cation exchange resins having either fluoroalkyl sulfonic acid groups or fluoroalkyl carboxyl groups or both; and inorganic oxides having an organic group bound thereto having either a sulfonic acid group or a carboxyl group or both. Particularly preferred solid acids are cation exchange resins having fluoroalkyl sulfonic acid groups and zeolite. It is not preferred to use the well-known sulfonated polyaromatic ion exchange resins having the framework made by copolymerization of styrene and divinylbenzene in the second reaction step of the methylenation process, because the deterioration of the activities of those resins occurs in a short length of the reaction time. The reasons seen to be that the condensation products such as diphenylmethane dicarbamates and polymethylene polyphenylcarbamates are easily adsorbed on the resins and cover the acidic points of the resins, since those resins have a lot of benzene rings which have a strong affinity for polar aromatic compounds such as these condensation products. On the other hand, this problem is not likely to occur with the cation exchange resins having fluroalkyl chains which are used in the present invention.

In the process of the present invention, these carboxylic acids and solid acids may be used either alone or in combination. There is no particular limitation on the amount in which these carboxylic acids and solid acids are used. If the reaction is carried out batchwise or if carboxylic acids are used in the flow process, the acids are preferably used in an amount of $10^{-3}$ to $10^4$ equivalents, more preferably $10^{-2}$ to $10^2$ equivalents, per equivalent of the methylene-amino group in the compounds having the methylene-amino bond. If the reaction is carried out in a flow reactor retaining a solid acid, the flow rate of the compound having the methylene-amino group preferably ranges from $10^{-3}$ to $10^4$ equivalents, more preferably from $10^{-2}$ to $10^3$ equivalents, per hour per liter of the solid acid. The carboxylic acid may be used in an excess amount so that it may also serve as a solvent.

The reaction temperature for the second reaction step of the methylenation process generally ranges from 40° to 200° C., preferably from 60° to 180° C., and more preferably from 70° to 160° C. The reaction pressure generally ranges from 0.1 to 20 kg/cm$^2$, preferably from 0.5 to 10 kg/cm$^2$ and more preferably from 0.8 to 5 kg/cm$^2$. The reaction period varies with the type and amount of the acid catalyst used, the reaction temperature, the amount of the compound present having the methylene-amino bond, the amount of the N-phenylcarbamate present, and the nature of the specific reaction process (whether batchwise, continuous or flow process). Usually, the reaction continues for a period of several minutes to several hours, preferably 3 minutes to 5 hours, more preferably 5 minutes to 1 hour, but in almost all cases, the reaction in the second reaction step of the methylenation process can be completed within one hour. The reaction may be performed batchwise or in a continuous manner. If the acid catalyst consists of only a carboxylic acid, the reaction liquor may simply be passed through a flow reactor held at a predetermined temperature. If the acid catalyst consists of a solid acid, either the batchwise or flow process may be employed, and in either case, the solid acid is preferably retained within the reactor, or the solid acid is separated by a solid-liquid separator that immediately follows the reactor and is then returned to the reactor. The solid acid may be retained within the reactor by either fluidizing the acid within the reaction liquor or by fixing a catalyst bed of the acid in the reactor. Whichever reaction process is used, the solid acid permits a very easy separation from the reaction solution. Therefore, if the solid acid is used alone, the desired diphenylmethane dicarbamate can be directly obtained from the second reaction step.

The reaction in the second reaction step of the methylenation process may be performed without solvents, but if desired, it may be carried out in the presence of a suitable solvent. Illustrative solvents include aliphatic or alicyclic hydrocarbons such as pentane, hexane, heptane, octane, nonane, decane, n-hexadecane, cyclopentane and cyclohexane; halogenated hydrocarbons such as chloroform, ethylene chloride, carbon tetrachloride, dichloroethane, trichloroethane and tetrachloroethane; alcohols such as methanol, ethanol, propanol and butanol; aromatic compounds such as benzene, toluene, xylene, ethylbenzene, monochlorobenzene, dichlorobenzene, bromonaphthalene, nitrobenzene, and o-, m- or p-nitrotoluene; ethers such as diethyl ether, 1,4-dioxane and tetrahydrofuran; esters such as methyl acetate, ethyl acetate and methyl formate; and sulfolanes such as sulfolane, 3-methylsulfolane and 2,4-dimethylsulfolane. Also usable are aliphatic carboxylic acids such as acetic acid and propionic acid, and halogenated aliphatic carboxylic acids such as monochloroacetic acid, dichloroacetic acid, trichloroacetic acid and trifluoroacetic acid. Acid anhydrides of these carboxylic acids may also be used. If an organic solvent is used in the first reaction step of the methylenation process, the same solvent is preferably used in the second reaction step of that process. Particularly preferred organic solvents are nitrobenzene, chlorobenzene, and dichlorobenzenes.

If a carboxylic acid is used in the second reaction step of the methylenation process, it is separated from the reaction mixture, and a condensation product containing the desired diphenylmethane dicarbamate and sometimes a small amount of its higher homolog (i.e., polymethylene polyphenylcarbamate) is obtained. As already mentioned, α-halogenated carboxylic acids are preferred carboxylic acids, and of the α-halogenated carboxylic acids, trichloroacetic acid and trifluoroacetic acid are particularly preferred. These acids have boiling points lower than the N-phenylcarbamate used as the starting material and the diphenylmethane dicarbamate formed as the reaction product, and therefore they can be easily separated from the reaction mixture. The carboxylic acid thus separated is preferably returned for further use in the second reaction step of the methylenation process either immediately or after being properly adjusted for its composition.

When the solid acid is used, the separation of the solid acid and the reaction solution can be effected by a simple treatment such as filtration. When the solid acid is used by a more desirable method, namely the flow reaction method involving the use of a fixed bed or fluidized bed requiring the solid acid to be retained inside the reactor, the reaction of this second step can be carried out without entailing any treatment for the separation of the solid acid from the reaction solution.

Therefore, the acid catalyst used in the second reaction step of the methylenation process, whether it is a solid acid or carboxylic acid, can be separated very easily from the reaction solution.

If the solvents other than the carboxylic acids listed above are used in the second reaction step of the methylenation process, they may optionally be separated by distillation, preferably under 200° C., so as to obtain the desired condensation product containing at least 80 mol % of diphenylmethane dicarbamate.

When this solvent is the same solvent that is used in the subsequent process of thermal decomposition, the solvent is not required to be separated from the resultant reaction mixture.

In the reaction mixture which is obtained as described above, there is generally entrained the N-phenylcarbamate. This N-phenylcarbamate may be partly or wholly separated from the reaction mixture by a suitable treatment such as, for example, distillation (preferably at temperatures not exceeding 200° C.) before the reaction mixture is subjected to the process of thermal decomposition. Otherwise, the reaction mixture still containing this N-phenylcarbamate may be subjected in conjunction with the condensation product to the process of thermal decomposition and the phenyl isocyanate resulting from the decomposition may be collected in the upper part of the decomposition reactor while it is rising from the decomposition mixture. This phenyl isocyanate may be seized with an alcohol so as to be recovered in the original form of N-phenylcarbamate.

The so-obtained condensation product of N-phenylcarbamates mainly consists of the dinuclear diphenylmethane dicarbamate and contains little or no trinuclear dimethylene triphenylcarbamates. The selectivity for the desired diphenylmethane dicarbamate is over 80%.

Now, the resultant condensation product which contains diphenylmethane dicarbamate in a concentration of at least 80 mol % is subjected to the process of thermal decomposition so as to be decomposed into MDI and an organic hydroxyl compound.

The process of thermal decomposition contemplated by the present invention is characterized by the steps of allowing a mixture comprising 1 to 50% by weight of the aforementioned condensation product and 99 to 50% by weight of a solvent having a boiling point in the range of 150° to 350° C. and being inactive to isocyanates to flow down into a reactor kept at temperatures in the range of 180° to 380° C. through the upper part of the reactor, causing the introduced mixture to come into counterflow contact with a carrier introduced upwardly into the reactor through the lower part thereof, allowing the resultant organic hydroxyl compound to be discharged in the form of vapor in conjunction with the carrier through the upper part of the reactor, and withdrawing the isocyanate solution through the lower end of the reactor.

In the thermal decomposition carried out in the manner described above, the liquid component introduced downwardly into the reactor is particularly desired to descend in the shape of a thin film within the reactor. It has been found that the thermal decomposition reaction proceeds at a high rate without entailing any significant formation of by-products to produce MDI in high yields with high selectivity when the liquid component is introduced in the desirable shape described above. The reactor to be used for this thermal decomposition, therefore, is desired to be a vertical cylindrical reactor. Preferably, this reactor is packed with a solid packing or a solid catalyst or both. As the solid packing, any of the packings which have found popular acceptance for use in distillation columns and absorption columns is advantageously used. Naturally, the solid packing may be in any of the forms in which such solid packings are commercially available at all. A particularly desirable solid packing is one made of a material of high thermal conductivity. The solid substance thus packed in the reactor not merly produces an effect of increasing the surface area of the liquid component flowing down the interior of the reactor but also serves as a desirable medium for imparting the heat for thermal decomposition to the liquid component. The solid catalyst is used in the form of a fixed bed and therefore, unlike any homogeneous catalyst system, is not required to be separated from the isocyanate solution. This fact constitutes an advantage for the commercialization of the process of thermal decomposition. The catalyst of this nature is effective in lowering the temperature of thermal decomposition and increasing the reaction rate. Particularly when the catalyst is in a metallic form, it has high thermal conductivity and, therefore, gives the notable convenience for providing the heat of thermal decomposition.

Examples of the catalyst advantagously used for thermal decomposition include rare earth elements, antimony, and bismuth in their respective simple form, oxides, sulfates, and salts of such elements; boron in its simple form and boron compounds; metals of the copper group, zinc group, aluminum group, carbon group, and titanium group in the Periodic Table of Elements and oxides and sulfates of such metals; and carbides and nitrides of the elements of the carbon group except for carbon, titanium group, vanadium group, and chromium group in the Periodic Table of Elements.

The solvent to be used in the process of thermal decomposition is required to be inactive to any isocyanates under the conditions of thermal decomposition and to have a boiling point under atmospheric pressure in the range of 120° to 350° C., preferably 150° to 300° C. Only for the sake of the thermal decomposition reaction itself, the solvent may possess a boiling point exceeding 350° C. The temperature range specified above is significant because this solvent must be separated from the resultant isocyanate solution. This separation is effected by distillation because this treatment is simple and effective. If the boiling point of the solvent is very high, then the temperature of distillation is proportionately high and the isocyanate is consequently suffers from secondary reactions. For the purpose of precluding these secondary reactions, therefore, the boiling point of the solvent under atmospheric pressure is desired to be not more than 350° C., preferably not more than 300° C.

The solvents satisfying this requirement include aliphatic, alicyclic, and aromatic substituted or unsubstituted hydrocarbons and mixtures thereof and also include certain types of oxygenated compounds such as ethers, ketones, and esters.

As preferred solvents, there may be cited alkanes such as nonane, decane, undecane, dodecane, tridecane, tetradecane, pentadecane, hexadecane, heptadecane, and octadecane and their corresponding alkenes; aromatic hydrocarbons or alkyl-substituted aromatic hydrocarbons such as cumene, diisopropyl benzene, diethyl benzene, ethyl toluene, dibutyl benzene, naphthalene, methyl naphthalene, ethyl maphthalene, and dodecyl benzene; aromatic compounds substituted with nitro group and halogens such as chlorobenzene, dichlorobenzene, trichlorobenzene, bromobenzene, dibromobenzene, chlorotoluene, dichlorotoluene, chloronaphthalene, bromonaphthalene, nitrobenzene, chloronitrobenzene, nitronaphthalene; polycyclic hydrocarbon compounds such as diphenyl, substituted diphenyl, diphenyl methane, terphenyl, anthracene, phenanthrene, various dibenzyl-toluene isomers, triphenyl methane, and tetrahydronaphthalene; ketones such as acetophenone and benzophenone; esters such as dibutyl phthalate, dihexyl phthalate, and dioctyl phthalate; ethers and thioethers such as diphenyl ether and diphenyl sulfide;

sulfoxides such as dimethyl sulfoxide and diphenyl sulfoxide; and nitriles such as benzonitrile.

A preferred embodiment resides in using an organic solvent in the process of methylenation and using an organic solvent of the same kind in the process of thermal decomposition. In this case, therefore, the mixture comprising the condensation product resulting from the process of methylenation and containing at least 80 mol % of diphenylmethane dicarbamate and an organic solvent is, in its unmodified form, in a form diluted with the same organic solvent, or in a form concentrated to a prescribed composition, subjected to the process of thermal decomposition. The solvent to be used herein is desired to be an aromatic compound substituted with a nitro group and/or a halogen. A particularly desirable solvent is a halogenated aromatic hydrocarbon such as chlorobenzene or dichlorobenzene.

During the thermal decomposition, the diphenylmethane dicarbamate is converted into a corresponding MDI and an organic hydroxyl compound. To prevent these products of the conversion from being recombined into the carbamate, the organic hydroxyl compound so produced in consequence of the reaction is desired to be separated from the reaction system. For the purpose of enhancing this separation, the carrier is introduced upwardly into the thermal decomposition reactor throuogh the lowerpart thereof. Inside the reactor, the carrier runs into counterflow contact with the liquid component which is flowing down the reactor interior. Then, the carrier is withdrawn from the reactor through the upper part thereof in conjunction with the vapor of the organic hydroxyl compound produced by the reaction. This carrier is desired to be preheated before introduction into the reactor.

Examples of the carrier which is used advantageously in this case include inert gases and hydrocarbon gases such as nitrogen, argon, helium, carbon dioxide, methane, ethane, propane, and butane. Other compounds which fulfil the function of the carrier described above include low boiling organic solvent such as halogenated hydrocarbons represented by dichloromethane, chloroform and carbon tetrachloride, lower hydrocarbons represented by pentane, hexane, heptane and benzene, and ethers represented by tetrahydrofuran and dioxane.

These carriers may be used either singly or in the form of mixtures of two or more members.

The carrier withdrawn from the reactor through the upper part thereof entrains the organic hydroxyl compound and, occasionally, part of the thermal decomposition solvent. Desirably, therefore, separation of this mixture into the individual components may be effected by passing the mixture through a condenser kept at suitable temperatures or by subjecting the mixture to distillation, for example. The organic hydroxyl compound is withdrawn from the reaction system, while the carrier and the thermal decomposition solvent are circulated back to the reactor.

The organic hydroxyl compound thus withdrawn from the reaction system is preferred to be sent back to be used again in the process for the production of N-phenylcarbamate.

This reaction of thermal decomposition is desirably carried out continuously at a temperature in the range of 180° to 380° C., under a vacuum, under atmospheric pressure, or under application of pressure. The duration of this reaction is generally in the range of several minutes to several hours, preferably 1 minute to 5 hours, more preferably 2 minutes to 2 hours, although it is variable with the kinds of the thermal decomposition solvent, packing or catalyst, and carrier, the shape of the reactor, or the reaction temperature.

The thermal decomposition, when performed under the conditions described above, proceeds quickly without entailing any appreciable formation of by-products and affords the isocyanates in high yields.

When the isocyanate solution is withdrawn from the reactor through the lower part thereof as described above, it is treated to expel the thermal decomposition solvent. This separation of the solvent from the isocyanate solution is desired to be effected by distillation. For the purpose of curbing possible degradation of the yield and purity of the produced isocyanate by secondary reactions, this separation by distillation is desired to be carried out at the lowest possible temperature, for example, below 180° C., preferably below 150° C., over the shorted possible period. In this case, the thermal decomposition solvent is preferably completely removed from the product. The isolation of the product from the solvent may be advantageously effected by distilling the mixture to expel part of the diphenylmethane diisocyanate in conjunction with the solvent and returning the distillates back to the treatment for separation and purification.

By carrying out the process of methylenation and the process of thermal decomposition of the present invention as described above, MDI can be economically produced with a high selectivity of at least 80%, preferably at least 90%, from N-phenylcarbamate and a methylenating agent as the raw materials. It has also been demonstrated that the method of this invention enjoys various outstanding characteristics which render the method commercially feasible.

Now, this invention will be described more specifically below with reference to working examples. It should be noted, however, that this invention is not limited by these examples.

In these examples, the reaction products were analyzed as by gas chromatography and high-speed liquid chromatography.

EXAMPLE 1

First, methylenation of ethyl N-phenylcarbamate was carried out by a continuous flow method. In the first step of reaction, there was used a complete mixture type system consisting of three overflow type glass reactors each having an inner volume of 3 liters and provided with a stirrer. This system was constructed so that the reaction solution overflowing the reactors of the upper stages would be introduced into the reactors of the next lower stages. The reactors were each maintained at 90° C. Into the reactor of the uppermost stage in the system, a solution containing ethyl N-phenylcarbamate in a concentration of 33% in nitrobenzene and preheated to 90° C. was introduced at a flow rate of 15 ml/min. At the same time, an aqueous 37% formaldehyde solution was introduced at a flow rate of 0.7 ml/min and an aqueous 55% sulfuric acid solution preheated to 90° C. was introduced at a flow rate of 18 ml/min respectively into the reactor. After the contents of the reactor had assumed a steady stage, the reaction solution was led into a two-layer separator, there to be continuously separated into a nitrobenzene layer and an aqueous sulfuric acid solution layer. The nitrobenzene solution was introduced downwardly into a counterflow-contact type multi-stage extraction column maintained at 90° C. and hot water at 90° C. was delivered upwardly into the extraction column to remove a trace of sulfuric acid. Then, the nitrobenzene solution was dehydrated by expelling a small amount of water from the solution in conjunction with a part of nitrobenzene by distillation under a vacuum.

The nitrobenzene layer was found, by analysis, to comprise 67.7% by weight of ethyl N-phenylcarbamate, 27.5% by weight of diethyl 4,4'-diphenylmethane dicarbamate, 2.3% by weight of diethyl 2,4'-diphenylmethane dicarbamate, 0.8% by weight and 1.2% by weight respectively of bis-(N-carboethoxyanilino)-methane and ethyl (N-carboethoxyanilinomethyl)-phenylcarbamate each possessing a methylene-amino bond, and 0.5% by weight of trinuclear triethyl dimethylenetriphenylcarbamate. The reaction of the second step was carried out by combining the nitrobenzene solution with trifluoroacetic acid of the same weight and introducing the resultant mixture upwardly into a cylindrical reactor 3 cm in inside diameter maintained at 80° C. The residence time was fixed at 20 minutes. After the contents of the reactor had assumed a steady state, the reaction solution was found by analysis to contain no compound having a methylene-amino bond. The reaction mixture was distilled to expel trifluoroacetic acid. Subsequently, nitrobenzene and unaltered ethyl N-phenylcarbamate was separated by distillation. The condensation product obtained as the residue of the distillation was composed of 90.55 mol % of diethyl 4,4'-diphenylmethane dicarbamate, 9.44 mol % of diethyl 2,4'-diphenylmethane dicarbamate, and 0.01 mol % of triethyl dimethylenetriphenylcarbamate.

Under application of heat, this condensation product was dissolved in a concentration of 10% by weight in ortho-dichlorobenzene. The resultant solution was preheated to 150° to 160° C., then led to the upper part of a decomposition reactor with 5 cm in inside diameter and 3 m in length maintained at 280° C., and sprayed downwardly into the reactor interior at a flow rate of 25 ml/min. The reactor was packed with Raschig rings of stainless steel. Through the lower part of the reactor, preheated nitrogen gas was continuously introduced upwardly at a flow rate of 3 Nl/min. The reactor was provided in the upper part thereof with a partial condenser adapted to condensate ortho-dichlorobenzene. To the tip of this condenser was connected an alcohol trap kept cooled at −50° C.

The reaction of decomposition was continuously carried out under a pressure of 15 kg/cm². Consequently, there was obtained an isocyanate solution containing no unaltered carbamate. The ethanol was recovered substantially quantitatively by the trap.

The solution was distilled under a vacuum at a temperature of not more than 100° C. to expel ortho-dichlorobenzene. Consequently, there was obtained an isocyanate mixture consisting of 89.2% of 4,4'-MDI, 9.3% of 2,4'-MDI, and 1.5% of dimethylene triphenyl isocyanate by weight ratio.

EXAMPLE 2

A reaction vessel of glass having an inner volume of 400 ml was charged with 230 g of an aqueous 45 wt % sulfuric acid solution, 50 g methyl N-phenylcarbamate, 5.5 g of an aqueous 37% formaldehyde solution, and 50 g of nitrobenzene as a solvent. The contents of the reaction vessel were stirred at 90° C. for two hours to effect reaction. Then, the resultant reaction mixture was separated into an organic layer and an aqueous layer. The organic layer was washed with hot water to remove a small amount of remaining sulfuric acid. Then, a small amount of water still contained in the organic layer was removed by azeotropic distillation with a part of nitrobenzene. When the resultant organic layer was analyzed, it was found that the conversion of methyl N-phenylcarbamate was 41%, the yield of dimethyl 4,4'-diphenylmethane dicarbamate was 32%, the yield of dimethyl 2,4'-diphenylmethane dicarbamate was 2.8%, and the yields of bis-(N-carbomethoxyanilino)-methane and methyl (N-carbomethoxyanilinomethyl)-phenylcarbamate each possessing a methylene-amino bond were respectively 2.9% and 3.3%. The analysis did not detect any trinuclear or higher compound.

No formaldehyde was detected in the organic layer.

Then, a reaction tube of stainless steel 10 mm in inside diameter and 30 cm in length was packed with beads of fluorinated sulfonic acid resin having the repeating units of the following formula:

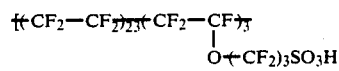

This reaction tube was kept at 120° C. and the aforementioned nitrobenzene solution was injected upwardly into the reaction tube through the lower part thereof at a flow rate of 0.5 ml/min. The reaction solution which was discharged through the upper end of the reaction tube was found to contain no compound possessing a methylene-amino bond. The reaction solution was distilled under a vacuum to expel nitrobenzene. The resultant reaction mixture consisted of 57% of methyl N-phenylcarbamate, 38% of dimethyl 4,4'-diphenylmethane dicarbamate, and 5% of dimethyl 2,4'-diphenylmethane dicarbamate. No trinuclear trimethyl dimethylenetriphenylcarbamate was contained in the reaction mixture.

By subjecting this mixture to vacuum distillation, most methyl N-phenylcarbamate distilling at 110° to 112° C./3 mmHg was recovered. As the residue of this distillation, there was obtained 23.1 g of a mixture consisting of 5.4% of methyl N-phenylcarbamate, 83.6% of dimethyl 4,4'-diphenylmethane dicarbamate, and 11% of dimethyl 2,4'-diphenylmethane dicarbamate by weight ratio. The condensation product consisted of 88.4 mol % of dimethyl 4,4'-diphenylmethane dicarbamate and 11.6 mol % of dimethyl 2,4'-diphenylmethane dicarbamate.

A solution of 23.1 g of this mixture in 200 g of n-pentadecane was introduced downwardly into a reaction tube of stainless steel maintained at 260° C. (2 cm in diameter and 2 m in length and packed with small particles of silicone carbide) at a flow rate of 3 ml/min and nitrogen gas heated to 250° C. was introduced upwardly into the reaction tube through the lower part thereof at a flow rate of 1 Nl/min.

The phenyl isocyanate produced by the decomposition of methyl N-phenylcarbamate was discharged in the form of vapor and led into a receptacle adapted to condense methanol. It was consequently recovered in its original form of methyl N-phenylcarbamate. A part of the n-pentadecane used as the solvent was entrained as a distillate.

The reaction solution produced in the amount of 210 g by the thermal decomposition was subjected to vacuum distillation to distill out the n-pentadecane at 98° to 100° C./0.5 mmHg. As the residue of this distillation, there was obtained 17.4 g of a mixture consisting of 88.4% of 4,4'-MDI and 11.6% of 2,4'-MDI.

EXAMPLE 3

This example represents a case in which the process of methylenation was carried out by using no organic solvent.

In a glass flask having an inner volume of 1 liter, 190 g of ethyl N-phenylcarbamate, 770 g of an aqueous 55 wt % sulfuric acid solution, and 19 g of an aqueous 37% formaldehyde solution were stirred at 90° C. for two hours to effect reaction. Then, the resultant reaction mixture was transferred into a separation funnel, to recover an organic layer and an aqueous layer separately of each other. The organic layer was washed with hot water and then treated with a rotary evaporator to expel water. The washings and the separated aqueous layer were combined and the combined water was treated with the rotary evaporator to expel a stated amount of water. Consequently, there was recovered 770 g of an aqueous 50 wt % sulfuric acid solution.

When the organic layer was analyzed, it was found that the conversion of ethyl N-phenylcarbamate was 38.5% and that the reaction produce was composed of 30.1% by weight of diethyl 4,4'-diphenylmethane dicarbamate, 4% by weight of diethyl, 2,4'-diphenylmethane dicarbamate, 1.9% by weight and 2.4% by weight respectively of bis-(N-carboethoxyanilino)-methane and ethyl (N-carboethoxyanilinomethyl)-phenylcarbamate each possessing a methylene-amino bond, and 0.9% by weight of trinuclear and higher compounds. No formaldehyde was detected in the organic layer.

Then this organic layer was combined with 150 g of trifluoroacetic acid and the resultant mixture was heated at 75° C. for 20 minutes to effect reaction. The resultant reaction mixture was distilled to expel trifluoroacetic acid. The reaction mixture thus obtained consisted of 60.2% of ethyl N-phenylcarbamate, 34.5% of diethyl 4,4'-diphenylmethane dicarbamate, 4.2% of diethyl 2,4'-diphenylmethane dicarbamate, and 1.1% of trinuclear triethyl dimethylenetriphenylcarbamate. No compound possessing a methylene-amino bond was detected.

By subjecting the condensation product to vacuum distillation, there was recovered 116 g of ethyl N-phenylcarbamate distilling at 108° to 110° C./1 mmHg. As the residue of the distillation, there was obtained 76.7 g of a condensation product. By the analysis of this condensation product, it was found that the selectivity of diethyl 4,4'-diphynelmethane dicarbamate was 87.5%, that of diethyl 2,4'-diphenylmethane dicarbamate was 10.7%, and that of triethyl dimethylenetriphenylcarbamate was 1.8% respectively. The combined selectivity of dinuclear diethyl diphenylmethane dicarbamate was 98.2%.

By distillation, 149 g of trifluoroacetic acid was recovered. This recovered acid could be put to reuse in its unmodified form.

A mixture consisting of 15% by weight of the condensation product and 85% by weight of ortho-dichlorobenzene was subjected to thermal decomposition by following the procedure of Example 1. The reaction tube used herein measured 2 cm in inside diameter and 4 m in length and was packed with Raschig rings made of aluminum and Dixon packing made of stainless steel. The liquid mixture preheated to 150° to 160° C. was sprayed downwardly into the reaction tube kept at 270° C. at a flow rate of 10 ml/min. Preheated nitrogen gas was introduced upwardly into the reaction tube at a flow rate of 1.5 Nl/min.

The reaction of decomposition was continuously carried out under a pressure of 8 kg/cm$^2$. As the result, there was obtained an isocyanate solution containing no unaltered carbamate. This solution was subjected to vacuum distillation at a temperature of not more than 100° C. to expel ortho-dichlorobenzene. Consequently, there was obtained an isocyanate mixture consisting of 87.5% of 4,4'-MDI, 10.7% of 2,4'-MDI, and 1.8% of dimethylenetriphenyl isocyanate.

EXAMPLE 4

The process of methylenation of ethyl N-phenylcarbamate was carried out by using the same apparatus as used in Example 1. Into the reactor of the uppermost stage in the system consisting of three reactors kept at 90° C., a solution containing ethyl N-phenylcarbamate in a concentration of 28% in ortho-dichlorobenzene preheated to 90° C. was introduced at a flow rate of 20 ml/min. At the same time, an aqueous 37% formaldehyde solution was introduced at a flow rate of 0.6 ml/min. and an aqueous 60% sulfuric acid solution was introduced at a flow rate of 15 ml/min respectively into the reactor. After the contents of the reactor had assumed a steady state, the reaction solution was led into a two-layer separator, there to be continuously separated into an ortho-dichlorobenzene layer and an aqueous sulfuric acid layer. The orthodichlorobenzene layer was introduced downwardly into a counterflow-contact type multi-stage extraction column kept at 90° C. and hot water at 90° C. was delivered upwardly into the extraction column to remove a trace of sulfuric acid. Then, a small amount of the water contained in the ortho-dichlorobenzene solution was removed by vacuum distillation with a part of ortho-dichlorobenzene.

When the ortho-dichlorobenzene solution was analyzed, it was found that the conversion of ethyl N-penylcarbamate was 52%, the selectivity of diethyl 4,4'-diphenylmethane dicarbamate and that of diethyl 2,4'-diphenylmethane dicarbamate were respectively 66.2% and 6.5%, and the selectivity of ethyl (N-carboethoxyanilinomethyl)-phenylcarbamate and that of trinuclear compounds (inclusive of compounds possessing a methylene-amino bond) were respectively 18.3% and 9%.

To the ortho-dichlorobenzene solution, trifluoroacetic acid was added to a concentration of 30% by weight. The resultant mixture was introduced upwardly into a cylindrical reaction vessel kept at 80° C. to effect the intermolecular transfer reaction of the second step. The residence time was fixed at 20 minutes. When the reaction solution was analyzed, it was found that no compound possessing a methylene-amino bond was present, that the selectivity of diethyl 4,4'-diphenylmethane dicarbamate and that of diethyl 2,4'-diphenylmethane dicarbamate were increased respectively to 84.5% and 8.2%, and that the selectivity of trinuclear triethyl dimethylenetriphenylcarbamate was decreased to 7.3%.

Then, this reaction solution was distilled to expel trifluoroacetic acid. The resultant ortho-dichlorobenzene solution was subjected to thermal decomposition by following the procedure of Example 1. In this case, the reaction tube had a length of 4 m and it was kept at 260° C. The phenyl isocyanate and ethanol which were formed in consequence of the thermal decomposition were withdrawn through the upper part of the reaction tube. This phenyl isocyanate was recovered substantially wholly in the form of ethyl N-phenylcarbamate.

The solution obtained through the lower part of the reaction tube was distilled at a temperature of not more than 100° C. to expel ortho-dichlorobenzene. Consequently, there was obtained an isocyanate mixture consisting of 83% of 4,4'-MDI, 8% of 2,4'-MDI, 7.3% of dimethylenetriphenyl isocyanate, and 1.7% of carbodiimide compounds derived from MDI.

EXAMPLE 5

The ortho-dichlorobenzene solution obtained at the end of the reaction of the first step in the process of methylenation obtained in Example 4 was introduced upwardly into a cylindrical reaction vessel kept at 150° C. to effect the intermolecular transfer reaction of the second step. This reaction tube was packed with the zeolite catalyst with high silica ratio to alumina. This zeolite was synthesized by the method of EPC Application No. 83113159.4 (produced by heating aluminum sulfate and silica zol in the presence of 1,8-diamino-4-aminomethyl octane and water at pH 12 at 170° C. for 48 hours thereby producing crystals and subsequently separating the crystals by filtration, washing, and drying). The residence time was fixed at 30 minutes. The condensation product obtained by this reaction comprised substantially the same composition as the condensation product obtained in Example 4. When the ortho-dichlorobenzene solution was subjected to thermal decomposition by following the procedure of Example 4, there was obtained an isocyanate having substantially the same composition as the isocyanate obtained in Example 4.

EXAMPLE 6

The nitrobenzene solution obtained at the end of the reaction of the first step in the process of methylenation in Example 1 was introduced upwardly into a cylindrical reaction vessel kept at 150° C. to effect the intermolecular transfer reaction of the second step. This reaction tube was packed with powdered anhydrous aluminum sulfate. The residence time was fixed at 30 minutes. The reaction which ensued produced a condensation product having substantially the same composition as the condensation product obtained in Example 1.

The nitrobenzene solution was distilled under a vacuum to expel nitrobenzene. The residue of the distillation was combined with ortho-dichlorobenzene of the same weight. The resultant solution was preheated to 150° to 160° C. and was introduced downwardly into the same thermal decomposition device as in Example 1. The reaction tube was kept at 260° C. and it was packed with Raschig rings made of copper. As a carrier, gasified n-pentane preheated to 240° C. was introduced upwardly into the reaction tube. The decomposition reaction was continuously carried out under a pressure of 12 kg/cm². Consequently, there was obtained an isocyanate having substantially the same composition as the isocyanate obtained in Example 1.

From the working examples cited above, it is noted that the method of the present invention permits economic production of MDI containing substantially no polymeric MDI or a small amount of polymeric MDI in high yields with high selectivity from N-phenylcarbamate.

While the invention has been described in detail and with reference to specific embodiments thereof, it will be apparent to one skilled in the art that various changes and modifications can be made therein without departing from the spirit and scope thereof.

What is claimed is:

1. A method for the manufacture of a diphenylmethane diisocyanate from a N-phenylcarbamate comprising:
    (A) a process of methylenation for the formation of a condensation product containing at least 80 mol % of a dinuclear diphenylmethane dicarbamate by the steps of
        (1) causing a methylenating agent to react upon at least 2 moles of a N-phenylcarbamate, based on 1 mole of the methylene group of said methylenating agent, in a liquid phase in the presence of an aqueous inorganic acid solution,
        (2) separating the resultant reaction mixture into the aqueous inorganic acid solution and an organic phase reaction mixture containing substantially none of said inorganic acid, and
        (3) subsequently treating said organic phase reaction mixture in the presence of a N-phenylcarbamate and a carboxylic acid having a pKa of not more than 4 in an aqueous solution at a temperature of 25° C. of a solid acid or an acid consisting of said two acids thereby converting a reaction intermediate possessing a methylene-amino bond and contained in said organic phase reaction mixture to a diphenylmethane dicarbamate, and
    (B) a process of thermal decomposition by the steps of allowing a mixture comprising 1 to 50% by weight of the condensation product obtained in said process of (A) and 99 to 50% by weight of a thermal decomposition solvent having a boiling point under atmospheric pressure in the range of 120° to 350° C. and being inactive to isocyanates to flow down into a reactor maintained at temperatures in the range of 180° to 380° C. through the upper part thereof, causing said mixture to come into counterflow contact with a carrier introduced into said reactor upwardly via the lower part thereof thereby producing an organic hydroxyl compound, allowing said organic hydroxyl compound to be discharged from said reactor in the form of vapor in conjunction with said carrier through the upper part thereof, and withdrawing the resultant isocyanate solution from said reactor through the lower part thereof.

2. A method according to claim 1, wherein said process of methylenation is carried out in the presence of an organic solvent.

3. A method according to claim 1, wherein said aqueous inorganic acid solution is an aqueous solution of 20 to 70% of sulfuric acid.

4. A method according to claim 1, wherein said N-phenylcarbamate for said process of methylenation is used in an amount of 2 to 10 moles per mole of the methylene group of said methylenating agent.

5. A method according to claim 1, wherein the reaction in said step of methylenation (A)-1) is carried out at a temperature in the range of 40° to 150° C. in the presence of an aqueous inorganic acid solution.

6. A method according to claim 1, wherein the reaction in said step of methylenation (A)-3) is carried out at a temperature in the range of 40° to 200° C. in the presence of a carboxylic acid or a solid acid or both of said acids.

7. A method according to claim 1, wherein said methylenating agent is an aqueous formaldehyde solution.

8. A method according to claim 2, wherein said organic solvent used in said process of methylenation has a boiling temperature of not more than 300° C. under atmospheric pressure and a mutual solubility of not more than 10% with water at room temperature.

9. A method according to claim 8, wherein said organic solvent used in said process of methylenation is an aromatic compound having at least one substituent selected from the group consisting of electron attracting groups and halogen atoms.

10. A method according to claim 9, wherein said electron attracting group is a nitro group.

11. A method according to claim 9, wherein said organic solvent used in said process of methylenation is selected from the group consisting of nitrobenzene, chlorobenzene, and dichlorobenzene.

12. A method according to claim 1, wherein said carboxylic acid used in said step of methylenation (A)-3) is at least one member selected from the group consisting of α-fluorocarboxylic acids, and α-chlorocarboxylic acids.

13. A method according to claim 12, wherein said α-fluorocarboxylic acid is trifluoroacetic acid.

14. A method according to claim 1, wherein said solid acid used in said step of methylenation (A)-3) is selected from the group consisting of (i) acid clay minerals, inorganic cation exchangers, and these acidic solid materials having undergone acid or protonation treatment; (ii) acidic metal oxides, mixed metal oxides, and these acidic solid materials having undergone acid or protonation treatment; (iii) organic cation exchange resins containing a fluoroalkyl sulfonic acid group or a fluoroalkyl carboxyl group or both; (iv) inorganic oxides having an organic group bonded thereto and containing a sulfonic acid group or a carboxyl group or both; and (v) acidic solid sulfates, nitrates, and phosphates.

15. A method according to claim 14, wherein said solid acid is a cation exchange resin containing a fluoroalkyl sulfonic acid group.

16. A method according to claim 14, wherein said solid acid is a zeolite.

17. A method according to claim 1, wherein said reactor used in said process of thermal decomposition is a cylindrical reactor packed with a solid packing material or a solid catalyst or both.

18. A method according to claim 2, wherein said organic solvent used in said process of methylenation is the same organic solvent that is used in said process of thermal decomposition.

19. A method according to claim 18, wherein said organic solvent is dichlorobenzene.

20. A method according to claim 1, wherein said carrier is selected from the group consisting of inert gases, hydrocarbons and halogenated hydrocarbons having a boiling point of not more than 150° C.

21. A method according to claim 1, wherein the N-phenylcarbamate is a compound having the general formula (I):

wherein R is an alkyl group having from 1 to 20 carbon atoms, preferably from 1 to 10 carbon atoms, aromatic group or an alicyclic group having 3 to 30 carbon atoms, preferably from 5 to 18 carbon atoms; R' is hydrogen or a substituent such as an alkyl group having from 1 to 20 carbon atoms, halogen atom, nitro group, cyano group, alkoxy group having from 1 to 20 carbon atoms or alicyclic group having from 3 to 20 carbon atoms, provided that these substituents are bonded at the ortho- or meta-position to the urethane group; r is an integer of 0 to 4; when r is 2 or more, R' may represent the same or different substituents; and at least one hydrogen in R may be substituted by any of the substituents defined above.

22. A method according to claim 3, wherein the inorganic acid solution is an aqueous solution of 40 to 60% of sulfuric acid.

23. A method as claimed in claim 21, wherein the N-phenylcarbamate is present in an amount in the range of 2.2 to 10 mols per mol equivalent of the methylene group of the methylenating agent.

24. A method as claimed in claim 1, wherein the step (A)-1) is carried out at a temperature in the range of 40 to 150° C. at a pressure in the range of 0.5 to 20 kg/cm².

25. A method as claimed in claim 24, wherein the step (A)-1) is carried out at a temperature in the range of 70 to 110° C. at a pressure in the range of 0.8 to 10 kg/cm².

* * * * *